US011446241B2

(12) United States Patent
Spallitta (10) Patent No.: US 11,446,241 B2
(45) Date of Patent: Sep. 20, 2022

(54) TREATMENT OF OPHTHALMOLOGICAL CONDITIONS WITH ACETYLCHOLINESTERASE INHIBITORS

(71) Applicants: Attillaps Holdings, Denver, CO (US); Frank Anthony Spallitta, Denver, CO (US)

(72) Inventor: Frank Anthony Spallitta, Denver, CO (US)

(73) Assignee: Attillaps Holdings Inc., Denver, CO (US)

( * ) Notice: Subject to any disclaimer, the term of this patent is extended or adjusted under 35 U.S.C. 154(b) by 0 days.

(21) Appl. No.: 16/954,798

(22) PCT Filed: Dec. 20, 2018

(86) PCT No.: PCT/US2018/066867
§ 371 (c)(1),
(2) Date: Jun. 17, 2020

(87) PCT Pub. No.: WO2019/126541
PCT Pub. Date: Jun. 27, 2019

(65) Prior Publication Data
US 2021/0085599 A1    Mar. 25, 2021

Related U.S. Application Data

(63) Continuation-in-part of application No. 15/319,897, filed as application No. PCT/US2015/036448 on Jun. 18, 2015, now Pat. No. 10,500,183, said application No. PCT/US2018/066867 is a continuation-in-part of application No. 14/444,748, filed on Jul. 28, 2014, now Pat. No. 10,709,135.

(60) Provisional application No. 62/608,435, filed on Dec. 20, 2017, provisional application No. 62/014,520, filed on Jun. 19, 2014, provisional application No. 61/859,572, filed on Jul. 29, 2013, provisional application No. 61/861,072, filed on Aug. 1, 2013, provisional application No. 61/953,290, filed on Mar. 14, 2014.

(51) Int. Cl.
| A61K 36/324 | (2006.01) |
| A61K 9/00 | (2006.01) |
| A61K 31/245 | (2006.01) |
| A61K 31/662 | (2006.01) |
| A61K 31/661 | (2006.01) |
| A61K 31/37 | (2006.01) |
| A61K 45/06 | (2006.01) |
| A61K 9/127 | (2006.01) |

(52) U.S. Cl.
CPC .......... *A61K 9/0048* (2013.01); *A61K 9/0014* (2013.01); *A61K 9/0053* (2013.01); *A61K 31/245* (2013.01); *A61K 31/37* (2013.01); *A61K 31/661* (2013.01); *A61K 31/662* (2013.01); *A61K 36/324* (2013.01); *A61K 9/127* (2013.01); *A61K 45/06* (2013.01)

(58) Field of Classification Search
None
See application file for complete search history.

(56) References Cited

U.S. PATENT DOCUMENTS

| 5,629,300 | A | 5/1997 | Boberg et al. |
| 5,952,372 | A | 9/1999 | McDaniel |
| 6,133,310 | A | 10/2000 | Parks |
| 6,258,378 | B1 | 7/2001 | Schneider et al. |
| 6,406,713 | B1 | 6/2002 | Janoff et al. |
| 6,680,308 | B1 | 1/2004 | Hassan |
| 7,919,522 | B2 | 4/2011 | Soll et al. |
| 8,128,968 | B2 * | 3/2012 | Gao ..................... A61K 9/00 424/725 |
| 8,440,240 | B2 | 5/2013 | Gao et al. |
| 8,475,818 | B2 | 7/2013 | Guerino et al. |
| 8,546,357 | B2 | 10/2013 | Akama et al. |
| 10,500,183 | B2 * | 12/2019 | Spallitta ............ A61K 31/473 |
| 10,709,135 | B2 * | 7/2020 | Spallitta ............ A61N 5/0616 |
| 11,045,442 | B2 | 6/2021 | Spallitta |

(Continued)

FOREIGN PATENT DOCUMENTS

| CN | 87103653 A | 12/1988 |
| CN | 1293977 A | 5/2001 |

(Continued)

OTHER PUBLICATIONS

Gao Y. et al. In Vitro and In Vivo Killing of Ocular Demodex by Tea Tree Oil. British J Ophthalmology 89:1468-1473, 2005. (Year: 2005).*
Mills, C. et al. Inhibition of Acetylcholinesterase by Tea Tree Oil. J of Pharmacy & Pharmacology 56:375-9, 2004. (Year: 2004).*
Dietrich J. et al. Pathophysiology of Meibomian Glands—An Overview. Ocular Immunology & Inflammation 29(4)803-810 May 2021. (Year: 2021).*
Bhreathnach R. et al. Feline Dermatology Irish Veterinary J 49(5)307-310, 1996. (Year: 1996).*
Agres (Sep. 29, 2011) "New Life for Old Drugs" Advantage Business Media. http://www.dddmag.com/articles/2011/07/new-life-old-drugs.

(Continued)

*Primary Examiner* — Ralph J Gitomer
(74) *Attorney, Agent, or Firm* — Leydig, Voit & Mayer, Ltd.

(57) ABSTRACT

Embodiments of the invention involve treating ophthalmology conditions by the topical or oral use of acetylcholinesterase inhibitors. By effectively reducing or eliminating the population of *Demodex* mites in affected areas and areas where *Demodex* mites may exist, this treatment achieves a more complete remission of clinical signs and symptoms of the ophthalmological afflictions than any previously described method. Embodiments of the invention are useful for treating ocular afflictions caused by *Demodex*-induced inflammatory eye conditions, including meibomian gland dysfunction, conjunctivitis, keratoconjunctivitis, hyperemia, blepharitis and dry eye disease.

18 Claims, 4 Drawing Sheets

(56) References Cited

U.S. PATENT DOCUMENTS

| | | |
|---|---|---|
| 2003/0040504 A1 | 2/2003 | Gans et al. |
| 2005/0143325 A1 | 6/2005 | Guzzo et al. |
| 2005/0256028 A1 | 11/2005 | Yun et al. |
| 2006/0084632 A1 | 4/2006 | Goyal et al. |
| 2007/0020304 A1 | 1/2007 | Tamarkin et al. |
| 2007/0287733 A1 | 12/2007 | Snorrason |
| 2008/0292560 A1 | 11/2008 | Tamarkin et al. |
| 2008/0299220 A1 | 12/2008 | Tamarkin et al. |
| 2009/0068255 A1 | 3/2009 | Yu et al. |
| 2009/0099135 A1 | 4/2009 | Enan |
| 2009/0214676 A1 | 8/2009 | Gao et al. |
| 2010/0099668 A1 | 4/2010 | Guerino et al. |
| 2010/0333221 A1 | 12/2010 | Chabriere et al. |
| 2011/0009457 A1 | 1/2011 | Gorgens et al. |
| 2011/0033395 A1 | 2/2011 | Kaoukhov et al. |
| 2011/0034471 A1 | 2/2011 | Held |
| 2011/0059988 A1 | 3/2011 | Heckeroth et al. |
| 2011/0150795 A1 | 6/2011 | Loing et al. |
| 2011/0288141 A1 | 11/2011 | Freehauf et al. |
| 2013/0095051 A1 | 4/2013 | Kaoukhov et al. |
| 2013/0131016 A1 | 5/2013 | Akama et al. |
| 2013/0131017 A1 | 5/2013 | Akama et al. |
| 2013/0131050 A1 | 5/2013 | Matsunaga et al. |
| 2013/0177662 A1 | 7/2013 | Msika et al. |
| 2013/0225516 A1 | 8/2013 | Soll et al. |
| 2013/0243886 A1 | 9/2013 | Hu et al. |
| 2013/0338197 A1 | 12/2013 | Mita et al. |
| 2013/0344128 A1 | 12/2013 | Gao et al. |
| 2014/0017216 A1 | 1/2014 | Klein et al. |
| 2015/0086596 A1 | 3/2015 | Spallitta |
| 2021/0069176 A1 | 3/2021 | Spallitta |
| 2021/0077559 A1* | 3/2021 | Spallitta ............... A61K 47/38 |
| 2021/0369698 A1 | 12/2021 | Spallitta |

FOREIGN PATENT DOCUMENTS

| | | |
|---|---|---|
| CN | 1771971 A | 5/2006 |
| EP | 2355790 A2 | 8/2011 |
| GB | 2419093 A | 4/2006 |
| WO | WO 2004/000337 A1 | 12/2003 |
| WO | WO 2006/040688 A2 | 4/2006 |
| WO | WO 2009/010754 A2 | 1/2009 |
| WO | WO 2009/030686 A1 | 3/2009 |
| WO | WO 2010/066639 A2 | 6/2010 |
| WO | WO 2013/078071 A1 | 5/2013 |
| WO | WO 2015/017328 A2 | 2/2015 |
| WO | WO 2015/195928 A1 | 12/2015 |

OTHER PUBLICATIONS

Akilov (2004) "Immune response in demodicosis", J. Eur. Acad. Dermatol. Venereol., 18(4):440-444.
Akilov et al. (2003) "Association between human demodicosis and HLA class I", Clin. Exp. Dermatol., 28(1):70-73.
Akilov et al. (2005) "A clinico-pathological approach to the classification of human demodicosis", J. Dtsch Dermatol Ges., 3(8):607-614.
Aquilina et al. (2002) "Ivermectin-responsive Demodex infestation during human immunodeficiency virus infection. A case report and literature review," Dermatology 205(4): 394-397.
Askin et al. (2010) "Comparison of the two techniques for measurement of the density of Demodex folliculorum: standardized skin surface biopsy and direct microscopic examination", Br. J. Dermatol., 162(5):1124-1126.
Assen et al. (2005) "Ivermectin: pharmacology and application in dermatology", International J. of Dermatology, 44(12):981-988.
Aycan et al. (2007) "Frequency of the appearance of *Demodex* sp. in various patient and age groups", Turkiye Parazitoloji Dergisi. 31(2):115-118.
Ayres, Jr. (1963) "Rosaceam Like Demodicidosis", Calif Med., 98(6):328-330.
Baima et al. (2002) "Demodicidosis revisited", Acta Derm Venereol., 82(1):3-6.
Banker et al. (1979) "Disperse Systems", Modern Pharmaceutics, Ch. 9, Marcel Dekker, Inc. New York, New York.
Banker et al. (1979) "Tablet Dosage Forms", Modern Pharmaceutics, Ch. 10, Marcel Dekker, Inc. New York, New York.
Barnett (Aug. 29, 2012) "That Rose in Your Cheeks Could Be Bacteria," ABC News Medical Unit, [Accessible on the Internet at: http://abcnews.go.com/blogs/health/2012/08/29/that-rose-in-your-cheeks-could-be-bacteria].
Basta-Juzbasić et al. (2002) "Demodex folliculorum in development of dermatitis rosaceiformis steroidica and rosacea-related diseases", Clin Dermatol., 20(2):135-140.
Beridze et al. (2009) "Cryotherapy in treatment of skin demodecosis", Georgian Med. News, (170):43-5.
Bhatia et al. (2006) "Dispelling the Mystery of Demodex", The Dermatologist, 15(1):38-41.
Bhreathnach et al. (1996) Feline Dermatology Irish Veterinary J 49(5)307-310.
Bikowski et al. (2009) "Demodex Dermatitis a Retrospective Analysis of Clinical Diagnosis and Successful Treatment with Topical Crotamiton", J. Clin Aesthet Dermatol., 2(1):20-25.
Boni (2000) "Rosacea, acne and other diseases of seborrhoic origin," Schweizerische Rundschau fur Medizin/Praxis 89(14): 566-568 & p. 570.
Bonnar et al. (1993) "The Demodex mite population in rosacea", J. Am Acad Dermatol. 28(3):443-448.
Borgo et al. (2009) "PCR analysis for Wolbachia in human and canine Demodex mites", Arch Dermatol Res., 301(10):747-752.
Casas et al. (2012) "Quantification of Demodex folliculorum by PCR in rosacea and its relationship to skin innate immune activation", Exp Dermatol., 21:906-910.
Castillo (Aug. 30, 2012) "Red skin condition rosacea may be due to bacteria in skin mites," CBS News. [Accessible on the Internet at http://www.cbsnews.com/8301-504763_162-57503771-10391704/red-skin-condition-rosacea-may-be-due-to-bacteria-in-skin-mites].
Crawford et al. (2004) "Rosacea: I. Etiology, pathogenesis, and subtype classification", J. Am Acad Dermatol., 51(3):327-341.
Cresce et al. (Jun. 2014) "The Quality of Life Impact of Acne and Rosacea Compared to Other Major Medical Conditions", J. Drugs Dermatol., 13(6):692-697.
Czepita et al. (2005) "Investigations on the occurrence as well as the role of Demodex folliculforum and Demodex brevis in the pathogensis of blepharitis," Klin Oczna. 107(1-3):80-2.
Czepita et al. (2007) "Demoodex folliculorum and Demodex brevis as a cause of chronic marginal blepharitis", Ann Acad Med Stetin., 53(1):63-67.
De Jaureguiberry et al. (1993) "Demodex folliculitis: A cause of pruritus during human immunodeficiency virus infection," Annales De Medecine Interne 144(1): 63-64.
Del Rosso et al. (Mar. 2013) "An Evaluation of the Potential Correlations Between Pathophysiologic Mechanisms, Clinical Manifestations, and Management of Rosacea", Cutis., 91(3 Suppl):1-8.
Demmler (1997) "Blepharitis. Demodex folliculorum, associated pathogen spectrum and specific therapy," Ophthalmologe. 94(3):191-196.
Dietrich et al. (May 2021) Pathophysiology of Meibomian Glands—An Overview. Ocular Immunology & Inflammation 29(4)803-810.
Dittrich (1966) "Synergistic Effect Between Vapors of C-8514/Schering 36268 and Dichlorvos Against the Carmine Spider Mite", 59(4):893-896.
Dolenc-Voljc et al. (2005) "Density of Demodex folliculorum in perioral dermatitis", Acta Derm Venereol., 85(3):211-215.
Efi Pasmatzi et al. (2009) "Rosacea-Like Demodicosis Induced by Topical Pimecrolimus: Immunohistochemical Evaluation of Inflammatory Infiltrate", Hospital Chronicles, 4(4):172-174.
Elston (2010) "Demodex mites: Facts and controversies", Clin Dermatol, 28(5):502-504.
Erbagci et al. (1998) "The significance of Demodex folliculorum density in rosacea", Int. J. Dermatol., 37(6):421-425.
European Office Action, dated Apr. 29, 2020, corresponding to European Patent Application No. 14832600, 5 pp.

(56) References Cited

OTHER PUBLICATIONS

European Office Action, dated Dec. 2, 2020, corresponding to European Patent Application No. 14832600, 6 pp.
Fell (1886) "Demodex Folliculorum in Diseased Conditions of the Human Face", Proceedings of the Ninth Annual Meeting of the American Society of Microscopists, 8:120-127.
Forstinger et al. (1999) "Treatment of rosacea-like demodicidosis with oral ivermectin and topical permethrin cream" J. Am. Acad. Dermatol., 41(5 Pt 1):775-777.
Forton et al. (1993) "Density of Demodex folliculorum in rosacea: a case-control study using standardized skin-surface biopsy", Br. J. Dermatol., 128:650-659.
Forton (1998) "Demodex-associated folliculitis", Am. J. Dermatopathol. 20(5):536-537.
Forton et al. (1998) "Demodex folliculorum and topical treatment: acaricidal action evaluated by standardized skin surface biopsy", Br. J. Dermatol., 138(3):461-466.
Forton et al. (1998) "Limitations of standardized skin surface biopsy in measurement of the density of Demodex folliculorum. A case report", Br. J. Dermatol., 139(4):697-700.
Forton et al. (2005) "Demodicosis and rosacea: epidemiology and significance in daily dermatologic practice", J. Am. Acad. Dermatol., 52(1):74-87.
Forton (2007) "Standardized skin surface biopsy: method to estimate the Demodex folliculorum density, not to study the Demodex folliculorum prevalence", J. Eur. Acad. Dermatol. Venereol., 21(9):1301-1302.
Forton (2011) "Papulopustular rosacea, skin immunity and Demodex: pityriasis folliculorum as a missing link," J. Eur. Acad. Dermatol. Venereol., 26(1):19-28.
Fulk et al. (1996) "Pilocarpine gel for the treatment of demodicosis—a case series", Optom. Vis. Sci., 73(12):742-745.
Gao et al. (2005) "In vitro and in vivo killing of ocular Demodex by tea tree oil," Br. J. Ophthalmol., 89(11):1468-1473.
Gao et al. (2007) "Clinical treatment of ocular demodecosis by lid scrub with tea tree oil", Cornea, 26(2):136-143.
Georgala et al. (2001) "Increased density of Demodex folliculorum and evidence of delayed hypersensitivity reaction in subjects with papulopustular rosacea", J. Eur. Acad. Dermatol. Venereol., 15(5):441-444.
Gillette (Sep. 5, 2012) "Bacteria-laden mites may cause rosacea," Dermatology Times, [Accessible on the Internet at: http://dermatologytimes.modernmedicine.com/dermatology-times/content/bacteria-laden-mites-may-cause-rosacea].
Goodman (Aug. 30, 2012) "Are Mites Causing Your Rosacea?," WebMD, LLC, [Accessible on the Internet at: http://www.webmd.com/skin-problems-and-treatments/news/20120830/are-mites-causing-your-rosacea].
Hom et al. (Jul. 2013) "Demodex", Optom. Vis. Sci., 90(7):e198-205.
Hsu et al. (2009) "Demodicosis: a clinicopathological study", J. Am. Acad. Dermatol., 60(3):453-462.
International Search Report with Written Opinion corresponding to International Patent Application No. PCT/US2014/048420, dated Nov. 14, 2014, 19 pages.
International Search Report with Written Opinion corresponding to International Patent Application No. PCT/US2015/036448, dated Sep. 16, 2015, 18 pages.
International Search Report with Written Opinion corresponding to International Patent Application No. PCT/US2018/066867, dated Mar. 8, 2019, 16 pages.
Ivanhoe Newswire (Dec. 11, 2007) "Something to Blush About, Medical Breakthroughs", Ivanhoe Newswire.
Ivy (1995) "Demodicidosis in childhood acute lymphoblastic leukemia; an opportunistic infection occurring with immunosuppression", J. of Pediatrics, 127(5):751-754.
Jansen et al. (1996) p. A3126 of "Demodex mites and their significance in facial dermatoses", Munchener Medizinische Wochenschrift 138(27): 483-487.
Jansen et al. (2001) "Rosacea-like demodicidosis associated with acquired immunodeficiency syndrome", 144(1):139-142.
Jarmuda et al. (2012) "Potential Role of Demodex Mites and Bacteria in the Induction of Rosacea," J of Medical Microbiology 61(11): 1504-1510.
Jesitus (2007) "Empirical treatment is key to identifying rosacea, other dermatoses", Dermatology Times.
Jio (Aug. 31, 2012) "Health & Beauty: Could These Tiny Mites Be Causing Your Rosacea?" Conde Nast, [Accessible on the Internet at: http://www.glamour.com/health-fitness/blogs/vitamin-g/2012/08/health-beauty-could-these-tiny].
Kennedy (2006) "CollaGenexwins FDA approval for Oracea", MarketWatch, Inc., [Accessible on the Internet at: http://www.marketwatch.com/story/collagenex-wins-fda-approval-for-oracea].
Kheirkhah et al. (2007) "Corneal manifestations of ocular demodex infestation", Am. J. Ophthalmol., 143(5):743-749.
Kligman et al. (2011) "Demodex folliculorum: Requirements for Understanding Its Role in Human Skin Disease", J. of Investigative Dermatology, 131:8-10.
Koo et al. (2012) "Ocular Surface Discomfort and Demodex: Effect of Tea Tree Oil Eyelid Scrub in Demodex Blepharitis," J. Korean Med Sci 2012, vol. 27, 1574-1579.
Kot et al. (2017) "Blepharitis and *Demodex* spp. Infection," Ophthalmology J 2(1):22-27.
Kulac et al. (2008) "Clinical importance of Demodex folliculorum in patients receiving phototherapy", Int. J. Dermatol., 47(1):72-77.
Kupiec-Banasikowska et al. (2007) "Rosacea", WebMD, LLC, [Accessible on the Internet at: http://emedicine.medscape.com/article/1071429-overview].
Lacey et al. (2007) "Mite-related bacterial antigens stimulate inflammatory cells in rosacea", Br. J. Dermatol., 157(3):474-481.
Lacey et al. (2009) "Under the lash: Demodex mites in human diseases", Biochem.(Lond), 31(4):2-6. Author manuscript provided.
Lacey et al. (2013) "Demodex quantification methods: Limitations of Confocal Laser Scanning Microscopy (CLSM)", Br. J. Dermatol., 169(1):212-213.
Larios et al. (2008) "Rosacea-like demodicidosis," Lancet Infect Dis., 8(12):804.
Lazaridou et al. (2010) "The potential role of microorganisms in the development of rosacea", J. of the German Society of Dermatology, 9:21-25.
Lee et al. (2007) "Granulomatous rosacea-like demodicidos", Dermatol. Online J., 13(4):9.
Li et al. (2010) "Correlation between ocular Demodex infestation and serum immunoreactivity to Bacillus proteins in patients with Facial rosacea", Ophthalmology, 117(5):870-877.
Liu et al. (2010) "Pathogenic role of Demodex mites in blepharitis," Curr Opin Allergy Clin Immunol. 10(5):505-510.
MacKenzie (Aug. 30, 2012) "Rosacea may be caused by mite feces in your pores," New Scientist, [Accessible on the Internet at: https://www.newscientist.com/article/dn22227-rosacea-may-be-caused-by-mite-faeces-in-your-pores/].
Manolette R Roque et al. (Nov. 5, 2015) "Demodicosis", WebMD, LLC, [Accessible on the Internet at URL: http://emedicine.medscape.com/article/1203895-overview].
McCarty (Mar. 15, 2013) "Bayer Sues Glenmark Over Patent for Rosacea Drug Finacea," Bloomberg L. P. [Accessible on the Internet at URL: http://www.bloomberg.com/news/articles/2013-03-15/bayer-sues-glenmark-over-patent-for-rosacea-drug-finacea].
Mills et al. (2004) "Inhibition of Acetylcholinesterase by Tea Tree Oil," J of Pharmacy & Pharmacology 56:375-9.
Moore (Aug. 31, 2012) "Rosacea May Be Caused by Bacteria Released by Tiny Mites Living on the Skin," Medical News Today, [Accessible on the Internet at: http://www.medicalnewstoday.com/releases/249664.php].
Moravvej et al. (2007) "Association of rosacea with demodicosis", Arch, Iran Med., 10(2):199-203.
Mumcuoglu et al. (2005) "The role of HLA A2 and Cw2 in the pathogenesis of human demodicosis", Dermatology, 210(2):109-114.

(56) References Cited

OTHER PUBLICATIONS

National Rosacea Society (May 3, 2004) "New Study Shows Role for Bacteria in Development of Rosacea Symptoms," NRS Press Release. [Accessible on the Internet at: http://www.rosacea.org/press/archive/20040503.php].

National Rosacea Society (2010) "Mites and Eye Symptoms," NRS Web Blog Thursday. [Accessible on the Internet at: http://www.rosacea.org/weblog/mites_and_eye_symptoms].

National Rosacea Society (Fall 2010) "NRS-Funded Studies Advance Knowledge of Rosacea's Causes," Rosacea Review, [Accessible on the Internet at: http://www.rosacea.org/rr/2010/fall/article_1.php].

National Rosacea Society (Sep. 5, 2012) "The Chicken, not the Egg?" National Rosacea Society, [Accessible on the Internet at: http://www.rosacea.org/weblog/the_chicken_not_the_egg].

National Rosacea Society (2016) "All About Rosacea," National Rosacea Society, [Accessible on the Internet at: http://www.rosacea.org/patients/allaboutrosacea.php].

NBC News (Aug. 29, 2012) "Tiny mites on your face may cause rosacea," NBC News, [Accessible on the Internet at URL: http://vitals.nbcnews.com/_news/2012/08/29/13554038-tiny-mites-on-your-face-may-cause-rosacea?lite].

New York Daily News (Sep. 5, 2012) "New discovery may hold clues to rosacea cure; Red bumps may be linked to mites living on the face," New York Daily News. [Accessible on the Internet at: http://www.nydailynews.com/life-style/health/new-discovery-hold-clues-rosacea-cure-red-bumps-linked-mites-living-face-article-1.1152511].

Nielsen et al. (1988) "Glycolamide esters as biolabile prodrugs of carboxylic acid agents: synthesis, stability, bioconversion, and physicochemical properties", J. of Pharmaceutical Sciences, 77:285-298.

NIH News (2007) "Lavender and Tea Tree Oils May Cause Breast Growth in Boys," NIH News [Accessible on the Internet at: http://www.nih.gov/news-events/news-releases/lavender-tea-tree-oils-may-cause-breast-growth-boys].

Norn (1970) "Demodex folliculorum. Incidence and possible pathogenic role in the human eyelid", Acta Ophthalmologica, Ch. VII, In, 48(S108):71-78.

O'Connell (Jul. 14, 2009) "Study finds cause of rosacea," The Irish Times [Accessible on the Internet at: http://www.irishtimes.com/news/health/study-finds-cause-of-rosacea-1.699476].

O'Reilly et al. (2011) "Demodex-associated bacterial proteins induce neutrophil activation", Br. J. Dermatol., 166(4):753-760.

O'Reilly et al. (2012) "Demodex-associated Bacillus proteins induce an aberrant wound healing response in a corneal epithelial cell line (hTCEpi)", Invest. Ophthalmol. Vis. Sci. 53(6):3250-3259.

O'Reilly et al. (2012) "Positive correlation between serum immunoreactivity to Demodex-associated Bacillus proteins and erythematotelangiectatic rosacea", Br. J. Dermatol., 167(5):1032-1036.

Pena et al. (2000) "Is demodex really non-pathogenic?", Rev Inst Med Trop Sao Paulo, 42(3):171-173.

Pitman (Aug. 30, 2012) "Researchers Claim to be Closer Towards Effective Treatment of Rosacea Cosmetics Design," William Reed Business Media SAS [http://www.cosmeticsdesign.com/Formulation-Science/Researchers-claim-to-be-closer-towards-effective-treatment-of-rosacea].

Pohanka (2012) "Acetylcholinesterase Inhibitors: A Patent Review 2008-Present," Expert Opinion on Therapeutic Patents 22(8): 871-886.

Press Trust of India (Aug. 30, 2012) "Rosacea may be caused by skin bacteria: study," Business Standard, [Accessible on the Internet at: http://www.business-standard.com/article/pti-stories/rosacea-may-be-caused-by-skin-bacteria-study-112083000384_1.html].

Prieto et al. (2002) "Effects of intense pulsed light on sun-damaged human skin, routine, and ultrastructural analysis", Lasers Surg. Med., 30(2):82-85.

PSMicrographs "Follicle mite (*Demodex folliculorum*)," PSmicrographs [Accessible on the Internet at: www.psmicrographs.co.uk/follicle-mite-demodex-folliculorum-/science-image/80016342].

Rather et al. (Jan.-Feb. 2014) "Human Demodex Mite: The Versatile Mite of Dermatological Importance," Indian J of Dermatology 59(1): 60-66.

Rebora (2002) "The management of rosacea", Am. J. Clin. Dermatol. 3(7):489-496.

Ríos-Yuil et al. (Mar.-Apr. 2013) "Evaluation of Demodex folliculorum as a Risk Factor for the Diagnosis of Rosacea in Skin Biopsies. Mexico's General Hospital (1975-2010)", Indian J Dermatol., 58(2):157. pp. 1-10.

Roihu et al. (1998) "Demodex mites in acne rosacea", J. Cutan Pathol., 25(10):550-552.

Román-Curto et al. (2012) "Demodicidosis simulating acute graft-versus-host disease after allogeneic stem cell transplantation in one patient with acute lymphoblastic leukemia", Transpl. Infect. Dis., 14:387-390.

Rufli et al. (1981) "The hair follicle mites *Demodex folliculorum* and *Demodex brevis*: biology and medical importance. A review", Dermatologica. 162(1):1-11.

Sahn et al. (1992) "Demodicidosis in a child with leukemia", J. Am. Acad. Dermatol., 27(5 Pt 2):799-801.

Sandoz, "Sandoz Launches First Generic Version of Metrogel® 1% in the US," Sandoz: A Novartis [Accessible on the Internet at: http://www.sandoz.com/media_center/press_releases_news/global_news/sandoz_launches_first_generic_version_of_metrogel_reg_1_in_the_us.shtml].

Sattler et al. (2012) "Non-invasive in vivo detection and quantification of Demodex mites by confocal laser scanning microscopy", Br. J. Dermatol., 167(5):1042-1047.

Schaller et al. (2003) "Demodex abscesses: clinical and therapeutic challenges", J. Am. Acad Dermatol., 49(5 Suppl):S272-S274.

Schmidt et al. (2004) "Demodex and rosacea, III: Treatment of Demodex mites associated with inflammatory rosacea", Cosmetic Dermatology, 17(10):655-658.

Schneider et al. (1999) "Metrifonate: A Cholinesterase Inhibitor for Alzheimer's Disease Therapy", CNS Drug Reviews, 5(1):13-26.

Science Daily (Aug. 29, 2012) "Bacterial Cause Found for Skin Condition Rosacea," Science Daily [Accessible on the Internet at URL: https://www.sciencedaily.com/releases/2012/08/120829195121.htm].

Sekizawa et al. (1989) "Environmental Health Criteria 79: Dichlorvos", World Health Organization. Geneva, Switzerland.

Shelley et al. (1989) "Unilateral demodectic rosacea", J. Am. Acad Dermatol., 20(5 Pt 2):915-917.

Sifferlin (Sep. 4, 2012) "Rosacea: Caused by Mite Poop in Your Facial Pores?" Time Magazine. [Accessible on the Internet at: http://healthland.time.com/2012/09/04/rosacea-caused-by-mite-poop-in-your-facial-pores/].

Spiegel et al. (1963) "Use of nonaqueous solvents in parenteral products", J. of Pharmaceutical Sciences, 52(10):917-927.

Stanislaw et al. (2012) "The potential role of Demodex folliculorum mites and bacteria in the induction of rosacea," J. of Medical Microbiology, 61:1504-1510.

Supplementary European Search Report corresponding to European Patent Application No. 14832600, dated Jun. 29, 2016, 11 pages.

Supplementary European Search Report corresponding to European Patent Application No. 15809417.7, dated Feb. 9, 2018, 5 pages.

Talghini et al. (Jul. 2014) "Demodex folliculorum and Skin Disease: A Case-Control Study", J. Med. Sci., 14(5):229-234.

Walton et al. (2000) "Studies in vitro on the relative efficacy of current acaricides for *Sarcoptes scabiei* var. hominis", Trans. Royal Chem. Soc., 94:92-96.

Wilkin et al. (2002) "Standard classification of rosacea: Report of the National Rosacea Society Expert Committee on the Classification and Staging of Rosacea", J. of the American Academy of Dermatology, 46:584-587.

Wood "Compendium of Pesticide Common Names; Classification of acaricides," [Accessible on the Internet at: http://alanwood.net/pesticides/class_acaricides.html] pp. 1-8 (Archived web page from Dec. 12, 2010).

Woods (2003) "It's Enough to Make Your Skin Crawl: Microscopic Mites May Be Linked to Acne, Thinning Hair and Other Skin (56) References Cited

OTHER PUBLICATIONS

Disorders," University of Florida's Institute of Food and Agricultural Sciences. [Accessible on the Internet at: http://entomology.ifas.ufl.edu/pestalert/acne.htm].

Wozniacka et al. (2005) "Topical application of 1-methylnicotinamide in the treatment of rosacea: a pilot study", Clin. Exp. Dermatol., 30(6):632-635.

Zahavi et al. (1970) "Sensitivity of acetylcholinesterase in spider mites to organo-phosphorus compounds", Biochemical Pharmacology, 19:219-225.

Zhao et al. (2010) "Retrospective analysis of the association between demodex infestation and rosacea", Arch. Dermatol. 146(8):896-902.

Zhao et al. (2011) "Facial dermatosis associated with Demodex: A case-control study", Journal of Zhejiang University-Science B. 12(12):1008-1015.

Zhao et al. (2011) "Influence of temperature and medium on viability of Demodex folliculorum and Demodex brevis", Exp. Appl. Acarol., 54:421-425.

Zhao et al. (2012) "A meta-analysis of association between acne vulgaris and infestation", Journal of Zhejiang University-Science B. 13(3):192-202.

\* cited by examiner

| Compounds | LT50 in Minutes | Average minutes to death | Total mites | LT50 |
|---|---|---|---|---|
| FCO | 181 | 198.02 | 51 | 26/51 |
| Tonka Bean (couramin) | 181 | 198.02 | 51 | 26/51 |
| Frankincense (boswellia sacra) | 24 | 26.71 | 51 | 26/51 |
| Mineral Oil | 50 | 50.78 | 51 | 26/51 |
| Wild Lettuce (lactucopicrin) | 494 | 497.51 | 121 | 61/121 |
| Malkangni Seed Oil (celastrus paniculatus) | 119 | 64.29 | 57 | 29/57 |
| Dichlorvos 1% water | 5 | 9.16 | 50 | 25/50 |
| Malathion 1% water | 113 | 110.34 | 56 | 28/56 |
| Malathion 1% oil | 388 | 379.06 | 50 | 25/50 |
| Metrifonate 1% water | 437 | 432.38 | 63 | 32/63 |
| Metrifonate 1% oil | 354 | | 50 | 25/50 |
| Physostigmine 1% water | 248 | 257.90 | 51 | 26/51 |
| Galantamine 1% water | 181 | 216.02 | 60 | 30/60 |
| Demacarium 1% water | 703 | | 65 | 33/65 |
| Donepezil 1% water | 539 | | 58 | 29/58 |
| Tacrine 1% water | 603 | | 50 | 25/50 |
| Diisopropyl fluorophosphate | 426 | | 58 | 29/58 |
| Echothiophate 1% water | 561 | | 63 | 32/63 |
| Rivastigmine 1% water | | | | |
| Neostigmine 1% water | No activity | | 19 | |
| Warfarin 1% water | No activity | | 51 | |
| Pyridostigmine 1% water | No activity | | 54 | |
| Edrophonium 1% water | No activity | | 52 | |
| Ambenonium 1% water | No activity | | 57 | |
| Distilled Water | No activity | | 59 | |
| Chloroquine 10% water | 2688 | | | 56/112 |
| Doxycycline 5% water | 1896 | | 56 | 28/56 |
| Huperzine A (natural) 1% water | 685 | | 62 | 31/62 |
| Huperzine A (synthetic) 1% water | 450 | | 57 | 29/57 |

FIG. 4

TREATMENT OF OPHTHALMOLOGICAL CONDITIONS WITH ACETYLCHOLINESTERASE INHIBITORS

This application is a U.S. National Stage Application filed under 35 U.S.C. § 371 of International Application No. PCT/US2018/066867, filed Dec. 20, 2018, which claims the benefit of priority to U.S. Provisional Patent Application No. 62/608,435 filed on Dec. 20, 2017. This application is a continuation-in-part application of U.S. patent application Ser. No. 15/319,897 filed Dec. 19, 2016, now U.S. Pat. No. 10,500,183, issued Dec. 10, 2019 (86-14 US) and Ser. No. 14/444,748 (41-14 US) filed Jul. 28, 2014. Ser. No. 15/319,897 is a national stage application of PCT/US15/36448 filed Jun. 18, 2015 which claims the benefit of U.S. Provisional App. No. 62/014,520 filed Jun. 19, 2014. Ser. No. 14/444,748 claims the benefit of U.S. Provisional App. Nos. 61/859,572 filed Jul. 29, 2013, 61/861,072 filed Aug. 1, 2013 and 61/953,290 filed Mar. 14, 2014. Each of these applications are hereby incorporated by reference in their entireties to the extent they are not inconsistent with the disclosure herein.

BACKGROUND

Provided herein are methods for treatment of various ophthalmological afflictions in humans employing topically applied or orally dosed acetylcholinesterase inhibitors and/or carbamates, such as ethyl carbamates to inactivate certain organisms associated with the ophthalmological affliction. For example, by reducing or eliminating *Demodex* organisms from affected hair follicles, skin, eyes, eyelids, eyelashes, or meibomian gland areas, the methods reduce clinical signs of the ophthalmological afflictions which are primarily due to allergic and inflammatory responses of the body to the *Demodex* organisms and bacteria that are associated or carried by the *Demodex* organism.

Eyelid involvement may be manifested by mild conjunctival irritation or inflammation of the meibomian (oil) glands on the eyelid margin. Chronic eyelid irritation can result in loss of eyelashes. Meibomian gland dysfunction caused by the irritation and inflammation can lead to chronic dry eye disease and/or blepharitis.

Although hypothesized as a root cause of dry eye associated with Meibomian gland dysfunction, *Demodex folliculorum* has yet to reach consensus and no commercially viable pharmacological solutions are available for treating *Demodex brevis* and *Demodex folliculorum* in the eyelid. Reaction to the presence or metabolic activity of *Demodex* mites in eyelash follicles has been discussed as a cause of blepharitis but previous studies where topical miticides other than acetylcholinesterase inhibitors have been used have shown inconsistent and marginal results. *Demodex* seems to play a role in meibomian gland dysfunction which can eventually cascade into chronic dry eye disease.

The etiology of dry eye disease is becoming increasingly well understood. Dry eye disease is progressive in nature, and fundamentally results from insufficient tear coverage on the surface of the eye. This poor tear coverage prevents healthy gas exchange and nutrient transport for the ocular surface, promotes cellular desiccation and creates a poor refractive surface for vision. Poor tear coverage typically results from: excessive evaporation of aqueous tear resulting from dysfunction of the meibomian glands. The meibomian gland at the rim of the eyelids inside the tarsal plate are responsible for the supply of meibum, an oily substance that prevents evaporation of the eye's tear film. If the flow of meibum is blocked by *Demodex* (or indirectly by an inflammatory response to *Demodex*), cylindrical dandriff caused by *Demodex*, or inflammation resulting from *Demodex* or bacteria proliferated by *Demodex*, a lack of meibum causes a cascading effect that leads to chronic dry eye disease. Low tear volume causes a hyperosmolar environment that induces an inflamed state of the ocular surface. This inflammatory response induces apoptosis of the surface cells which in turn prevents proper distribution of the tear film on the ocular surface so that any given tear volume is rendered less effective. This initiates a vicious positive feedback loop cycle where more inflammation can ensue causing more surface cell damage, etc. Additionally, the neural control loop, which controls reflex tear activation, is disrupted because the sensory neurons in the surface of the eye are damaged. As a result, fewer tears are secreted and a second vicious cycle develops that results in further progression of the disease because fewer tears cause nerve cell loss, which results in even fewer tears, etc.

There is a wide spectrum of treatments for dry eye disease, however, none provides substantial efficacy for treatment of the condition. Treatment options include: artificial tear substitutes, ointments, gels, warm compresses, environmental modification, topical cyclosporine, omega-3 fatty acid supplements, punctal plugs and moisture chamber goggles. Patients with severe disease may further be treated with punctal cautery, systemic cholinergic agonists, systemic anti-inflammatory agents, mucolytic agents, autologous serum tears, PROSE scleral contact lenses and tarsorrhaphy. Despite these treatment options, dry eye disease continues to be considered one of the most poorly treated diseases in ophthalmology. Accordingly, it would be desirable to have a more effective treatment for dry eye.

Conventionally, dry eye is treated with the frequent use of artificial tears or other lubricating eye drops. Artificial tears usually are the first step in dry eye treatment. RESTASIS® eye drops are the most commonly prescribed pharmaceutical intervention for dry eye (RESTASIS® (Cyclosporine Ophthalmic Emulsion) 0.05%) and contains cyclosporine which is an immunosuppressant. Cyclosporine can increase tear production that has been reduced by inflammation in the eye(s). RESTASIS® eye drops are used to treat chronic dry eye that may be caused by inflammation. Ocular rosacea is characterized by ocular manifestations such as dry eye, tearing and burning, swollen eyelids, recurrent styes and potential vision loss from corneal damage. There is a need in the art for safe and effective treatment of ophthalmological conditions, specifically *Demodex*-induced inflammatory eye conditions such as Meibomian gland dysfunction, conjunctivitis, keratoconjunctivitis, hyperemia, dry eye, and blepharitis. Accordingly, provided herein are various treatments that specifically target this *Demodex*-induced mechanism.

SUMMARY OF THE INVENTION

Provided herein are treatment methods for *Demodex*-induced inflammatory eye conditions, including that alleviate, abrogate, or otherwise reduce or stop any one or more clinical symptoms associated with *Demodex*-induced inflammatory eye conditions by administering or applying specific acetylcholinesterase inhibitors.

Embodiments of the invention described herein involve treating ophthalmological afflictions by the topical, intraocular or oral use of one or more than one specified acetylcholinesterase inhibitors. By effectively reducing or eliminating the population of *Demodex* mites in affected areas and areas where *Demodex* mites may exist, this treatment achieves a more complete remission of clinical signs and symptoms of the ophthalmological afflictions than any previously described method. Embodiments of the invention are useful for treating ophthalmological afflictions related to *Demodex*-induced inflammatory eye conditions, including meibomian gland dysfunction, conjunctivitis, keratoconjunctivitis, hyperemia (excess blood supply to the eye), blepharitis and dry eye disease.

An exemplary method embodiment comprises a step of orally-administering or topically-applying to an individual having the ophthalmological affliction, including *Demodex*-induced inflammatory eye conditions, an acetylcholinesterase inhibitor in a dosage sufficient to inactivate *Demodex brevis* and/or *Demodex folliculorum* mites from hair follicles, skin, eyes, eyelids, eyelashes, or meibomian glands of the individual, resulting in amelioration or cessation of the manifestations of allergic and/or inflammatory responses to the mites that cause symptoms and signs of the ophthalmological affliction in the individual. In an embodiment, the acetylcholinesterase inhibitor is not an organophosphate, including acetylcholinesterase inhibitors and organophosphates described in WO 2015/017328 and WO 2015/195928 including, but not limited to, dichlorvos, metrifonate, malathion, iisopropyl fluorophosphate and echothiophate. In an exemplary embodiment, the acetylcholinesterase inhibitor is topically applied. In an embodiment, for example, the topically-applied acetylcholinesterase inhibitor is formulated in a saline solution, carrier lotion, cream, soap, wash, shampoo, gel, impregnated wipe, swab or via a spoolie brush. Preferably, the administration is around the eye and regions adjacent thereto, but not directly into the eye.

Optionally, a concentration of the acetylcholinesterase inhibitor in the topically-applied lotion, cream, soap, wash, shampoo, saline solution or gel is about 0.001 to 1 percent by weight or about 0.01 to 1 percent by weight. In an exemplary embodiment, a concentration of the acetylcholinesterase inhibitor in the topically-applied saline solution, lotion, cream, soap, wash, shampoo or gel is a lowest concentration effective for killing the *Demodex* mites. In one embodiment, a dosage of acetylcholinesterase inhibitor in the topically-applied lotion, cream, soap, wash, shampoo, saline solution or gel is less than about 1 50 mg/kg of body mass or between about 0.01 mg per kg of body mass and 50 mg/kg of body mass. In an exemplary embodiment, a dosage of acetylcholinesterase inhibitor in the topically-applied saline solution, lotion, cream, soap, wash, shampoo or gel is a lowest dose effective for killing the *Demodex* mites. Optionally, the topically-applied acetylcholinesterase inhibitor is encapsulated inside microliposomes before being formulated into the carrier saline solution, lotion, cream, soap, wash, shampoo or gel.

In general, methods of the invention include those where the topically-applied acetylcholinesterase inhibitor is applied to said hair follicles, skin, eyes, eyelids, eyelashes, or meibomian glands areas affected by the ophthalmological affliction. In certain embodiments, however, the topically-applied acetylcholinesterase inhibitor is further applied to areas not affected by the ophthalmological affliction. For example, in one embodiment, the topically-applied acetylcholinesterase inhibitor is applied to the hair follicles, skin, eyes, eyelids, eyelashes, or meibomian glands areas of the body where *Demodex brevis* and/or *Demodex folliculorum* mites exist. In an exemplary embodiment, the topically-applied acetylcholinesterase inhibitor is applied to all areas.

Optionally, methods of the invention further comprise a step of applying the acetylcholinesterase inhibitor to the individual's clothing, linens or both clothing and linens. Such application is useful, for example, for preventing the individual's clothing or linens from being a source of *Demodex* mites to reintroduce onto the individual's skin. Similarly, methods of the invention optionally further comprise a step of orally-administering or topically-applying the acetylcholinesterase inhibitor to others having contact with the individual in a dosage sufficient to fill and eliminate *Demodex brevis* and/or *Demodex folliculorum* mites from hair follicles and/or skin of the others. For example, in embodiments, the others comprise household members, children, spouses, partners, family members or domestic pets.

In an exemplary embodiment of the methods of the invention, the topically-applied acetylcholinesterase inhibitor is applied to the hair follicles, skin, eyes, eyelids, eyelashes, or meibomian glands of the individual. In one embodiment, for example, the topically-applied acetylcholinesterase inhibitor penetrates an outer layer of the skin of the individual, thereby exposing the *Demodex brevis* and/or *Demodex folliculorum* mites present below the outer layer of the skin in the eyelid to the acetylcholinesterase inhibitor. In one embodiment, for example, the topically-applied acetylcholinesterase inhibitor penetrates to a subdermal region of the eyelid of the individual, thereby exposing the *Demodex brevis* and/or *Demodex folliculorum* mites present in and around the meibomian glands to the acetylcholinesterase inhibitor. Certain formulations of the topical acetylcholinesterase inhibitor useful with the methods of the invention optionally comprise one or more compositions that increase a permeability of the skin, such as dimethyl sulfoxide (DMSO).

In an exemplary embodiment, the topically-applied acetylcholinesterase inhibitor is applied to affected skin areas at least once and not more than twice daily for a period of about two to twelve weeks. In one embodiment, the topically-applied acetylcholinesterase inhibitor is applied to the affected areas and/or to non-affected areas during a first application period, thereby killing and eliminating adult *Demodex brevis* and/or *Demodex folliculorum* mites from the hair follicles, skin, eyes, eyelids, eyelashes, or meibomian glands. In one embodiment, the topically-applied acetylcholinesterase inhibitor is further applied to the affected areas and/or to non-affected areas during a second application period, thereby filling and eliminating from the hair follicles, skin, eyes, eyelids, eyelashes, or meibomian glands of the individual *Demodex brevis* and/or *Demodex folliculorum* mites that have matured from a larval form and/or an egg form present on and/or in the skin during the first application period. In one embodiment, the topically-applied acetylcholinesterase inhibitor is further applied to the affected areas and/or to non-affected areas during a third application period, thereby filling and eliminating from the hair follicles, skin, eyes, eyelids, eyelashes, or meibomian glands of the individual *Demodex brevis* and/or *Demodex folliculorum* mites that have matured from a larval form and/or an egg form present on and/or in the skin and/or the hair follicles during the first application period and/or the second application period.

Optionally, the first application period and the second application period are separated by at least five but no more than ten days. Optionally, the first application period and the second application period are separated by at least seven days. In an exemplary embodiment, the first application period and the second application period are separated by a time sufficient to allow the larva form to mature into an adult form and/or to allow the egg form to mature into the adult form.

Optionally, the second application period and the third application period are separated by at least five but no more than ten days. Optionally, the second application period and the third application period are separated by at least seven days. In an exemplary embodiment, the second application period and the third application period are separated by a time sufficient to allow the larva form to mature into an adult form and/or to allow the egg form to mature into the adult form.

In exemplary embodiments, the acetylcholinesterase inhibitor is orally-administered or topically-applied in a continued intermittent regime sufficient for prophylactic control of *Demodex* mite population in the hair follicles, skin, eyes, eyelids, eyelashes, or meibomian glands of the individual.

In another embodiment, the acetylcholinesterase inhibitor is orally-administered. In a specific embodiment, for example, the orally-administered acetylcholinesterase inhibitor is administered as an oral dose of the acetylcholinesterase inhibitor of about 1 50 mg per kg of body mass or less or between about 0.01 mg per kg of body mass and 50 mg per kg of body mass. In an exemplary embodiment, the orally-administered acetylcholinesterase inhibitor is administered as an oral dose of the acetylcholinesterase inhibitor of a lowest dose effective for killing the *Demodex* mites. In certain embodiments, the orally-administered acetylcholinesterase inhibitor is formulated as a prodrug or pharmaceutically acceptable salt.

Optionally, the orally-administered acetylcholinesterase inhibitor is administered as a daily dose of 10 mg per kg of body mass. Optionally, the orally-administered acetylcholinesterase inhibitor is administered as a daily dose of 7.5 mg per kg of body mass. Optionally, the orally-administered acetylcholinesterase inhibitor is administered as a three times per day dose of 5 mg per kg of body mass. Optionally, the orally-administered acetylcholinesterase inhibitor is repeated about two to four times with spacing of three to seven days between them. In embodiments where the administration is confined to a local region around the eye, lower doses may be used.

In various embodiments, the elimination of the *Demodex brevis* and/or *Demodex folliculorum* mites from hair follicles, skin, eyes, eyelids, eyelashes, or meibomian glands of the individual results in a reduction in population of one or more bacteria in the eyes, eyelids, eyelashes of the individual. For example, in some embodiments, the allergic and/or inflammatory responses to the mites result from a presence of one or more bacteria associated with the mites in the hair follicles, skin, eyes, eyelids, eyelashes, or meibomian glands of the individual. In specific embodiments, the one or more bacteria comprise one or more bacteria from the genus *Staphylococcus* or from the genus *Bacillus*. For example, in one embodiment, the one or more bacteria comprise *Bacillus oleronius* bacteria. In one embodiment, for example, the one or more bacteria comprise *Staphylococcus epidermidis* bacteria. Optionally, the one or more bacteria are present in a digestive system of the *Demodex brevis* and/or *Demodex folliculorum* mites.

Another exemplary method for treating an ophthalmological affliction comprises a step of topically-applying to an individual having the ophthalmological affliction an active ingredient in a dosage sufficient to fill and eliminate *Demodex brevis* and/or *Demodex folliculorum* mites from hair follicles, skin, eyes, eyelids, eyelashes, or meibomian glands of the individual, resulting in cessation of the manifestations of allergic and/or inflammatory responses to the mites that cause symptoms and signs of the ophthalmological affliction in the individual, wherein the topically-applied active ingredient is applied to hair follicles, skin, eyes, eyelids, eyelashes, or meibomian glands areas affected by the ophthalmological affliction and to skin areas not affected by the ophthalmological affliction. In a specific embodiment, the topically-applied active ingredient is applied to all facial skin of the individual, thereby filling and eliminating the *Demodex brevis* and/or *Demodex folliculorum* mites from all facial skin of the individual. Again, methods of the invention are useful, for example, for treating ocular conditions including meibomian gland dysfunction, blepharitis and dry eye disease. In an exemplary embodiment, the ophthalmological condition is caused by, exacerbated by or otherwise comorbid with an infestation of the skin and/or hair follicles by *Demodex* mites.

In an aspect, the acetylcholinesterase inhibitor is a reversible inhibitor. Compounds that are reversible competitive or noncompetitive inhibitors of cholinesterase include those having therapeutic uses, including: Carbamates, Physostigmin, Neostigmine, Pyridostigmine, Ambenonium, Demecarium, Rivastigmine, Phenanthrene derivatives, Galantamine, Caffeine—noncompetitive (also an Adenosine receptor antagonist)[13][14], Piperidines, Donepezil, Tacrine, also known as tetrahydroaminoacridine (THA'), Edrophonium, Huperzine A[15][16], Ladostigil, Ungeremine[17], and Lactucopicrin.

In an aspect, the acetylcholinesterase inhibitor is a quasi-reversible inhibitor. Compounds which function as quasi-irreversible inhibitors of cholinesterase tend to have use as pesticides. These include organophosphates and carbamates. Examples of organophosphates include: Echothiophate, Diisopropyl fluorophosphates, Cadusafos, Chlorpyrifos, Dichlorvos, Dimethoate, Metrifonate (irreversible), Malathion and Parathion. Examples of carbamates include: Aldicarb; Bendiocarb; Bufencarb; Carbaryl; Carbendazim; Carbetamide; Carbofuran Carbosulfan Chlorbufam; Chloropropham, Ethiofencarb; Formetanate; Methiocarb; Methomyl Oxamyl Phenmedipham, Pinmicarb; Pirimicarb; Propamocarb; Propham, Propoxur; Huperzine A; Galantamine; Onchidal Coumarins.

In another embodiment, the acetylcholinesterase inhibitor corresponds to a compound currently used in medicine, including those having an established safety profile in humans. Examples include: Aricept; Aricept ODT; Cognex; donepezil; Exelon; galantamine; Namzaric; Razadyne; rivastigmine; tacrine; phospholine; neostigmine; parathion malathion; dyflos; physostigmine; endrophonium; pyridostigmine; ecothiapate.

To further reduce the possibility of unwanted side effects, provided herein are methods that confine the amount and location of the acetylcholinesterase inhibitor to regions that provide the most benefit. In the case of the ophthalmological treatments provided herein, the application may be a topical administration to an eye region of the individual. Optionally, the eye region corresponds to an area of between at least 1 cm and 10 cm around an outermost perimeter defined by the eye, eyelid, eyebrow and eyelashes. In this manner, the inhibitor is confined to a region around the eye, thereby effectively treating the Meibomian glands, and mite-containing regions adjacent thereto that would otherwise tend to result in a relatively quick mite recovery/migration, while avoiding direct application to the eye.

Also provided herein is a method of treating an individual having a *Demodex*-induced ophthalmological affliction of Meibomian gland dysfunction, the method comprising the steps of: applying to the individual in need thereof an acetylcholinesterase inhibitor in a dosage sufficient to inactivate *Demodex brevis* mites and/or *Demodex folliculorum* mites from hair follicles, eyelids, eyelashes and Meibomian glands in and around an eye region; wherein a sufficient amount of *Demodex brevis* mites and/or *Demodex folliculorum* mites are inactivated to ameliorate or cease manifestations of allergic and/or inflammatory responses to the mites that cause symptoms or signs of Meibomian gland dysfunction. Although some variation in the precise amount of inactivation is tolerated by the instant methods, inactivation may refer to at least 50%, at least 70%, at least 90%, or at least 95% of the relevant mite population that is killed, unable to mature, and/or unable to effectively reproduce.

The allergic and/or inflammatory responses to *Demodex* may be manifested as Meibomian gland dysfunction, conjunctivitis, keratoconjunctivitis, hyperemia dry eye or blepharitis, wherein administration of an acetylcholinesterase inhibitor to inactivate *Demodex brevis* and/or *Demodex folliculorum* mites in an eye region reduces or eliminates allergic and/or inflammatory responses to the mites that cause symptoms and signs of the ophthalmological affliction in the individual.

The application may be a topical administration to an eye region of the individual. The "eye region" may be quantifiably defined as corresponding to an area of between at least 1 cm and 10 cm around an outermost perimeter defined by the eye, eyelid, eyebrow and eyelashes, and any subranges thereof.

Statements Regarding Chemical Compounds and Nomenclature

In an embodiment, a composition or compound used with the methods of the invention is isolated or purified. In an embodiment, an isolated or purified compound is at least partially isolated or purified as would be understood in the art. In an embodiment, the composition or compound of the invention has a chemical purity of 95%, optionally for some applications 99%, optionally for some applications 99.9%, optionally for some applications 99.99%, and optionally for some applications 99.999% pure.

Many of the compounds used in the methods of the invention contain one or more ionizable groups, Ionizable groups include groups from which a proton can be removed (e.g., —COOH) or added (e.g., amines) and groups which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The term "carbamate" generally refers to an organic compound derived from carbamic acid ($NH_2COOH$), such as $NR_2R_3COOR_1$:

In an aspect, each of the groups R1-R3 are independently selected to correspond to any of the R groups of the chemicals listed herein. In an aspect, any of R1-R3 are hydrogen.

Examples of carbamates for use with the methods described herein include, but are not limited to, neostigmine, rivastigmine, meprobamate, carisoprodol, felbamate, tybamate. Preferred carabamates are those that have been demonstrated to have miticidal or insecticidal capabilities and that can be provided to a mite on or in hair follicles, skin, eyes, eyelids, eyelashes, or meibomian glands at a level sufficient to inactivate or kill the mite without permanently adversely affecting the host patient. The carbamate may be a naturally occurring compound, such as a purified and isolated naturally occurring compound. Alternatively, the carbamate may be a synthetically produced carbamate, as known in the art. Any of the compounds provided herein may be provided in the form of a derivative, prodrug, or a pharmaceutically acceptable salt thereof.

In an aspect, the carbamate is selected from the group consisting of: aldicarb, bendiocarb, bufencarb, carbaryl, carbendazim, carbetamide, carbofuran, carbosulfan, chlorbufam, chloropropham, ethiofencarb, formetanate, methiocarb, methomyl, oxamyl, phenmedipham, pinmicarb, pirimicarb, propamocarb, propham, propoxur, butocarboxim, carbanolate, promacyl, thiocarboxime, thiofanox, benomyl, and metolcarb or a derivative, prodrug or pharmaceutically acceptable salt thereof.

In an aspect, the carbamate is an ethyl carbamate of the form=ethyl. R2 and R3 are optionally independently selected as hydrogen.

The compounds used in the methods of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

Pharmaceutically acceptable salts comprise pharmaceutically-acceptable anions and/or cations. As used herein, the term "pharmaceutically acceptable salt" can refer to acid addition salts or base addition salts of the compounds in the present disclosure. A pharmaceutically acceptable salt is any salt which retains at least a portion of the activity of the parent compound and does not impart significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, -32-cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalacturonic, propionic, salicylic, stearic, succinic, sulfamic, sulfanlic, sulfonic, sulfuric, tannic, tartaric, teoclic, toluenesulfonic, and the like. Pharmaceutically acceptable salts may be derived from amino acids, including but not limited to cysteine. Other pharmaceutically acceptable salts may be found, for example, in Stahl et al., Handbook of Pharmaceutical Salts: Properties, Selection, and Use, Wiley-VCH; Verlag Helvetica Chimica Acta, Zurich, 2002. (ISBN 3-906390-26-8). Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl''$, $Br''$), sulfate, acetates (e.g., acetate, trifluoroacetate), ascorbates, aspartates, benzoates, citrates, and lactate.

Also provided herein are methods of treating an individual having a Demodex-induced inflammatory eye condition. The method may comprise the steps of: applying to the individual in need thereof an acetylcholinesterase inhibitor in a dosage sufficient to inactivate Demodex brevis mites and/or Demodex folliculorum mites from an eye region of the individual, wherein the eye region includes one or more of hair follicles, eyelids, eyelashes and Meibomian glands in and around an eye region, including such that a sufficient amount of Demodex brevis mites and/or Demodex folliculorum mites are inactivated to ameliorate or cease manifestations of allergic and/or inflammatory responses to the Demodex mites that cause the inflammatory eye condition. This sufficient amount, depending on the sensitivity of the individual, may correspond to an at least 50%, 70%, 90% or 95% elimination, including in and around the eye region and/or a whole body decrease.

The inflammatory eye condition may correspond to one or more of: Meibomian gland dysfunction, dry eye, blepharitis, conjunctivitis, keratoconjunctivitis, or hyperemia.

For any of the applications described herein, the application may be a topical administration to the eye region of the individual, preferably avoiding application directly to the eye surface.

The eye region may correspond to an area of between at least 1 cm and 10 cm around an outermost perimeter defined by the eye, eyelid, eyebrow and eyelashes.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Inactivate" is used broadly herein to refer to the functional ability to decrease the impact of Demodex brevis and/or Demodex folliculorum mites. For example, the inactivation may be by death of the mite. Alternatively, the inactivation may refer to the inability of the mite to reproduce, so that the mite die off occurs as the mites age and die without reproduction. So long as the treatment leads to an adverse effect on the Demodex brevis and/or Demodex folliculorum mites that corresponds to improved clinical outcome, such as symptom improvement, the treatment is considered herein to inactivate Demodex brevis and/or Demodex folliculorum mites.

"Efficiently transported" refers to the ability of the treatment agent to act against mites that are located beneath the skin surface, such as into an epidermal or subdermal region so that the mites are timely inactivated.

"Substantially all" refers to, unless defined in the contrary, at least 90%, at least 95% or at least 99% of the relevant population, so in the context of Demodex mites, it refers to inactivation (e.g., killed or eliminated or otherwise unable to propagate) and/or application to hair (number) or skin (surface area).

As used herein, "Demodex" refers to D. folliculorum and D. brevis mites, including Demodex mites in humans that may contribute to a Demodex-induced inflammatory eye condition in humans.

D. folliculorum and D. brevis mites may play a role in ophthalmological conditions. An increased Demodex population has been observed in patients with ophthalmological afflictions. For most people, Demodex mites live harmlessly in the hair follicles, skin, eyelids, eyelashes, or meibomian glands as a result of either down-regulating host immunity or simply dodging host immune defenses. There is continual debate within the ophthalmology community as to whether or not they are the causative agents of such ophthalmological diseases as meibomian gland dysfunction, dry eye disease and blepharitis (inflammation of the eyelids).

Human beings are the one and only host of these ubiquitous mites [1]. In fact, these two mites are considered to be the most common ectoparasite of humans [6]. Women tend to have a higher rate of Demodex infections [5]. The rate of infestation also seems to be correlated with age, with 84% of people at age 60 harboring mites and increasing to 100% in those 70 years and older [7]. Whether those that are immunocompromised are more susceptible to higher infestation rates is unknown, though some studies indicate that AIDs and leukemia patients may be more prone to greater than average numbers [5].

The mites are most commonly found in the scalp, face and upper chest area, with D. folliculorum exhibiting a predilection for the hair follicles and D. brevis for the sebaceous ducts and meibomian glands at the rim of the eyelids (the sebaceous ducts transfer the waxy sebum that lubricates the skin and hair from the sebum glands; the meibomian glands are a special type of such gland) [4][5]. D. folliculorum are a communal bunch, tending to congregate in the follicle area of the hair or eyelashes with their posterior ends protruding from the follicular pores. D. brevis, on the other hand, tend to be more solitary and will occupy the sebaceous glands singly [6]. Both species are tiny, less than 0.4 mm, with elongated, clear bodies and four pairs of stout legs. D. brevis is usually a tad shorter, ~0.1 mm, than *D. folliculorum*. They both have ridged scales along their cephalothorax and sharp, piercing teeth [6].

Short-lived creatures, a mite's life cycle from egg to larva to adult lasts from 14-18 days. Adults emerge from the follicles and ducts to reproduce at the surface of the skin where females will then deposit eggs in the sebaceous glands. Larva will mature via two nymphal stages in the glands until entering the follicles and ducts as adults to begin the cycle anew [6]. It is hypothesized that both species of mites feed upon sebum as a primary food source but may also munch on follicular and glandular epithelia. They are thought to be obligate ectoparasites, incapable of living outside their human host.

Some studies have discovered a greater than average mite density, greater than five mites per $cm^2$, do seem to play a role in skin diseases for patients [6]. Researchers have suggested that blockage of the hair follicles and sebaceous ducts by mites may result in epithelial hyperplasia, elicit a phagocytic, granulomatous reaction or bring about an inflammatory response due to their waste products [5]. The fact that treatment with certain antibiotics can reduce the severity of meibomian gland dysfunction, blepharitis, dry eye disease strongly suggests a microbial component to mite-related diseases.

In 2007, researchers isolated from *D. folliculorum* a bacterium *Bacillus oleronium* that provoked inflammatory responses in 73% of rosacea patients but only 29% of controls [21]. These results suggest that patients with rosacea including ocular rosacea were sensitized to the bacteria and may be immunologically sensitive to the mites, bacteria or both [21].

Two antigenic proteins found on the bacterium's cell surface in particular appeared to be responsible for the inflammatory response by stimulating peripheral blood mononuclear cell proliferation; one 83 kDa protein showed similarity with heat-shock proteins while the other 62 kDa protein shared amino acid sequence homology with a protease enzyme found to be involved signal transduction as well as carbohydrate metabolism [21]. Stronger proof of the pathogenic role of *B. oleroniusin* ocular rosacea may also be found in the sensitivity of the bacterium to many antibiotics proven to be effective in the treatment of rosacea, specifically tetracycline, doxycycline and minocycline [21].

In an exemplary embodiment, an acetylcholinesterase inhibitor is administered topically to a patient with an active ophthalmological condition in which the underlying cause is a *Demodex* mite. Because the target organisms, *Demodex brevis* and *Demodex folliculorum*, are ectoparasites in the mite family, an effective treatment must be capable of eradicating the entire lifecycle of such a microscopic insect, including egg, larval, and adult stages. For this reason, this embodiment treats such patients with several doses. Such spacing allows time for *Demodex* eggs to hatch into immature mites that are killed before they can mature into egg-producing adults. After the acetylcholinesterase inhibitor carries out its miticidal activity on *Demodex brevis* and *Demodex folliculorum* organisms, inflammatory responses to them begin to diminish but remnants of the dead mites still elicit some flushing and lesion formation until the cleanup processes of the body remove them, a process requiring six to twelve weeks. During this initial phase of acetylcholinesterase inhibitor administration, conventional ophthalmological medications such as artificial tear substitutes, ointments, gels, warm compresses, environmental modification, topical cyclosporine, omega-3 fatty acid supplements, punctal plugs and moisture chamber goggles can be utilized in combination treatment with acetylcholinesterase inhibitor compounds. Patients with severe disease may further be treated with punctal cautery, systemic cholinergic agonists, systemic anti-inflammatory agents, mucolytic agents, autologous serum tears, PROSE scleral contact lenses and tarsorrhaphy can optionally be employed to suppress early flareups and to give early clinical response. No such medications are needed to treat manifestations of the ophthalmological condition after six to twelve weeks have elapsed. After prolonged intervals of freedom from symptoms, should classic signs begin to reappear, treatment can be repeated. The acetylcholinesterase inhibitor is formulated into a cosmetically-acceptable topical saline solution, lotion, cream, shampoo, or gel and applied especially to hair follicles, skin, eyes, eyelids, eyelashes, surrounding the eyes and any area possibly inhabited by *Demodex brevis* and *Demodex folliculorum*. Because of the well-known barrier effect the skin presents to the penetration of topical medications, such a route of treatment with acetylcholinesterase inhibitor is anticipated to require once or twice daily applications for as long as twelve to six weeks to achieve sufficient follicle penetration and effective miticidal activity. A topical formulation that could achieve this effect would contain about 5% or less of the acetylcholinesterase inhibitor. The lesser the percentage of the acetylcholinesterase inhibitor that can be used while still receiving the miticidal effect and successfully treating the ocular condition is ideal for limiting any possible side effects of the chemical. Further, full facial treatment is optionally useful for preventing reintroduction of the mites onto facial skin and glands.

Figure 1:
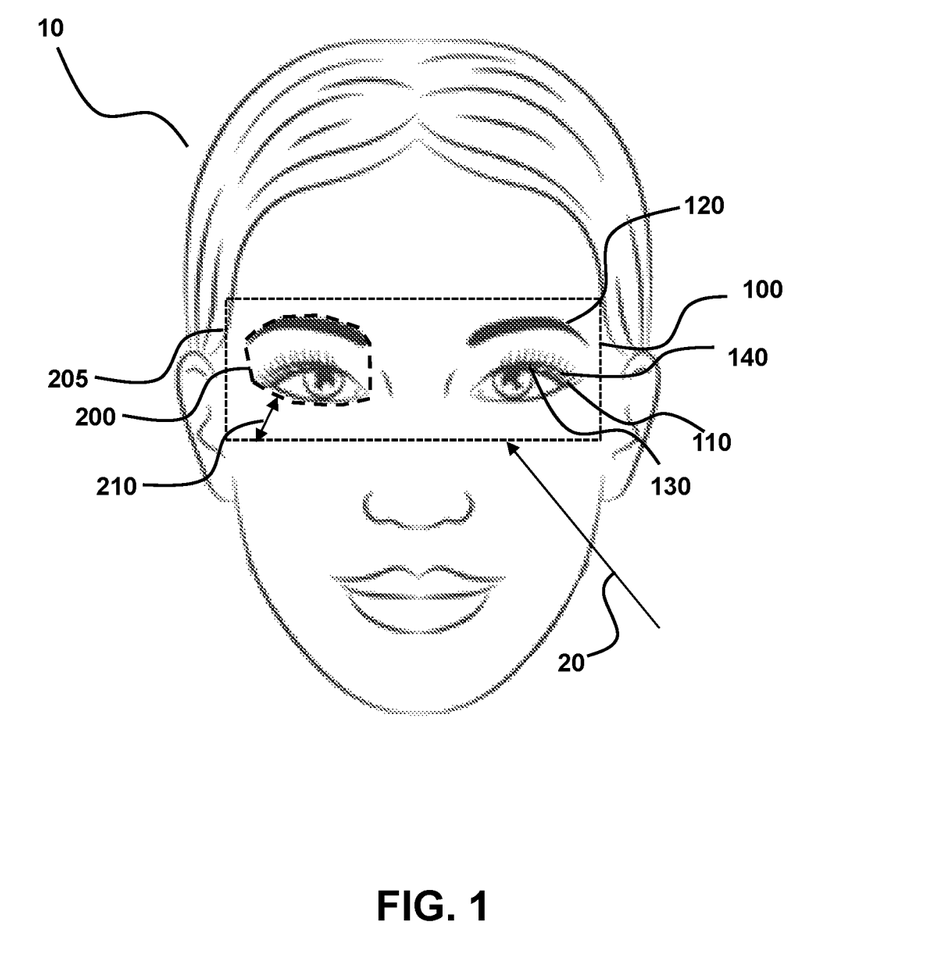
FIG. 1 summarizes a topical administration method to an eye region of an individual in need of treatment.

Referring to FIG. 1, a method of treating an individual 10 having a *Demodex*-induced ophthalmological affliction of Meibomian gland dysfunction, the method comprising the steps of: applying to the individual in need thereof an acetylcholinesterase inhibitor (indicated by arrow 20) in a dosage sufficient to inactivate *Demodex brevis* mites and/or *Demodex folliculorum* mites from hair follicles 100, eyelids 110, eyebrows 120, eyelashes 130 and Meibomian glands 140 in and around an eye region. In this manner, a sufficient amount of *Demodex brevis* mites and/or *Demodex folliculorum* mites are inactivated to ameliorate or cease manifestations of allergic and/or inflammatory responses to the mites that cause symptoms or signs of Meibomian gland dysfunction.

The allergic and/or inflammatory responses may be manifested by dry eye or blepharitis, and the symptoms related thereto. The application may be by a topical administration of acetylcholinesterase inhibitor 20 to an eye region 205 of the individual 10. Optionally, the eye region may be quantifiably defined, such as corresponding to an area of the eye region 205, including a distance 210, such as between at least 1 cm and 10 cm around an outermost perimeter 200 defined by the eye, eyelid, eyebrow and eyelashes. For clarity, the eye region 205 is illustrated as rectangular in shape, but the invention provided herein is compatible with any shape and region size, although it is preferable to control mite population in the area around the glands 140 so as to avoid relatively fast natural mite migration back to the glands 140 (or region adjacent thereto) with corresponding manifestation of unwanted clinical system. Accordingly, the methods provided herein, upon completion, may be characterized as ameliorating or cessation of symptoms and signs of the ophthalmolgical affliction of at least 30 days-6 months, and any range therein.

Figure 2:
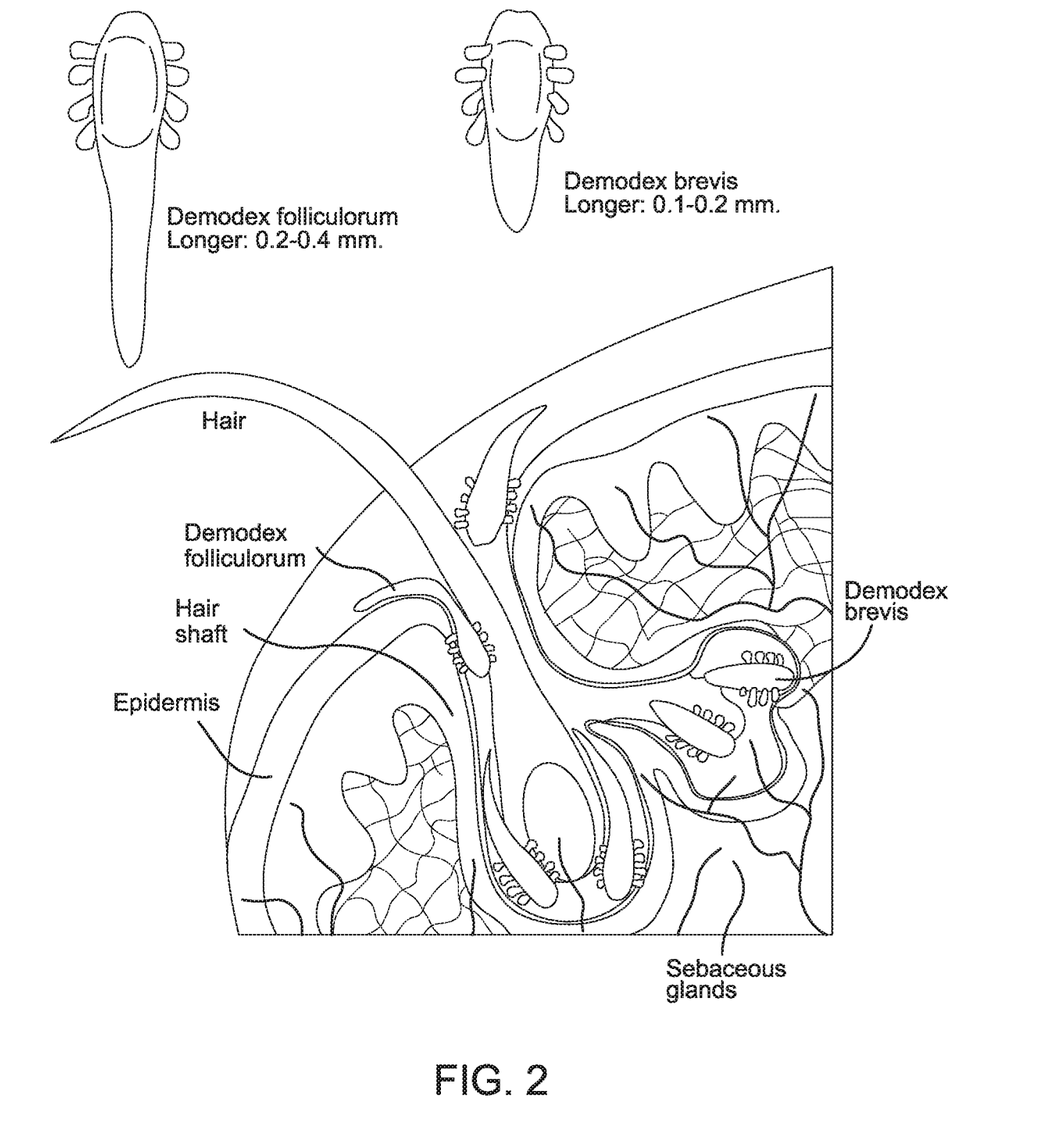
FIG. 2 is an illustration of Demodex folliculorum and Demodex brevis mites, including relative sizes and locations in the skin, hair follicles and glands.
Figure 3:
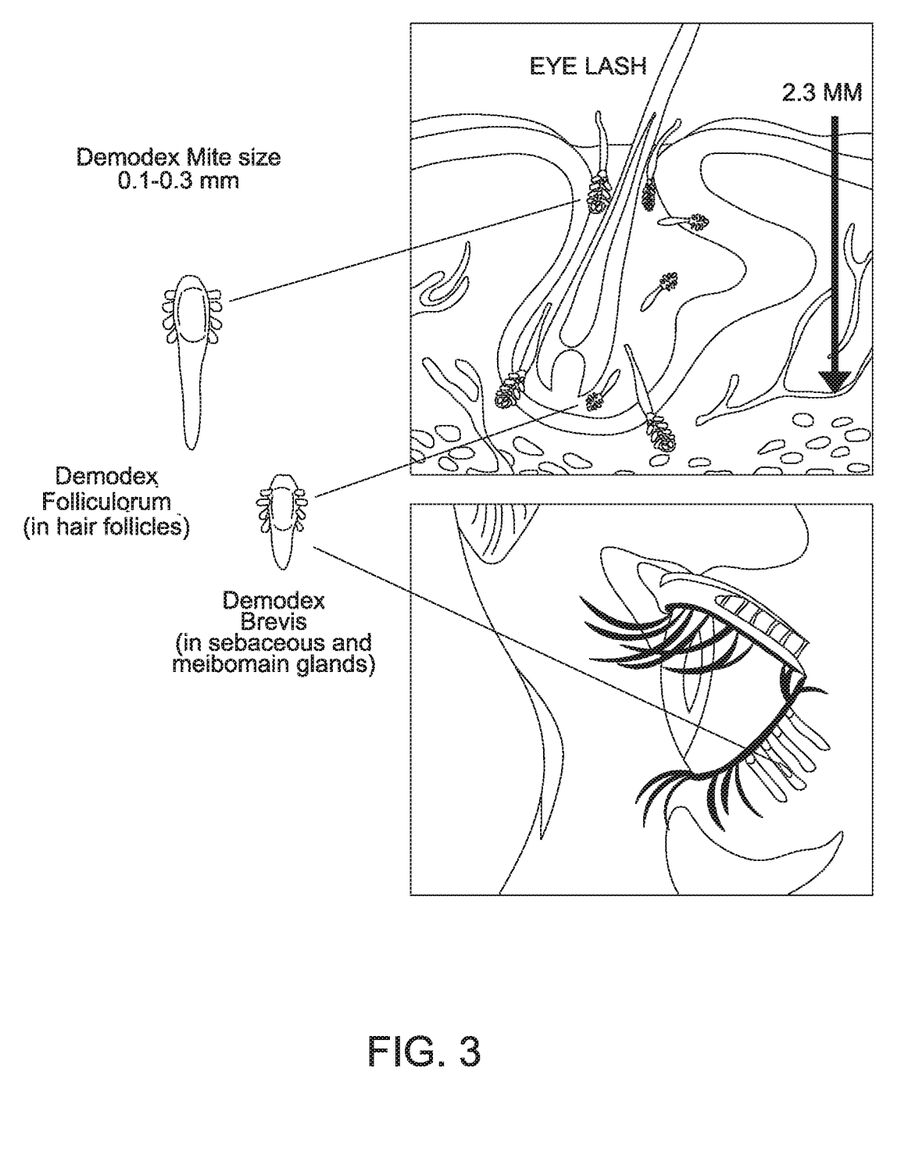
FIG. 3 illustrates Demodex mites in the eye region, including eye lash and meibomian glands.

FIGS. 2-3 illustrate the *Demodex brevis* and *folliculorum* mites in the skin area generally and the eye region, respectively, demonstrating the need to ensure treatment applications are able to achieve sub-dermal penetration.

Medical Use of Carbamates:

Urethane (ethyl carbamate) was once produced commercially in the United States as an antineoplastic agent and for other medicinal purposes. It was found to be toxic and largely ineffective. It is occasionally used as a veterinary medicine.

In addition, some carbamates are used in human pharmacotherapy, for example, the cholinesterase inhibitors neostigmine and rivastigmine, whose chemical structure is based on the natural alkaloid physostigmine. Other examples are meprobamate and its derivatives like carisoprodol, felbamate, and tybamate, a class of anxiolytic and muscle relaxant drugs widely used in the 60s before the rise of benzodiazepines, and still used nowadays in some cases.

The cholinesterase inhibitors neostigmine and rivastigmine may be efficacious if they have similar miticidal capabilities compared to many other carbamate compounds.

Drug class and mechanism: Rivastigmine is an oral medication used to treat patients with Alzheimer's disease. Rivastigmine is in a class of drugs called cholinesterase inhibitors that also includes tacrine (Cognex), donepezil (Aricept), and galantamine (Razadyne—formerly known as Reminyl). Cholinesterase inhibitors inhibit (block) the action of acetylcholinesterase, the enzyme responsible for the destruction of acetylcholine. Acetylcholine is one of several neurotransmitters in the brain, chemicals that nerve cells use to communicate with one another. Reduced levels of acetylcholine in the brain are believed to be responsible for some of the symptoms of Alzheimer's disease.

Figure 4:
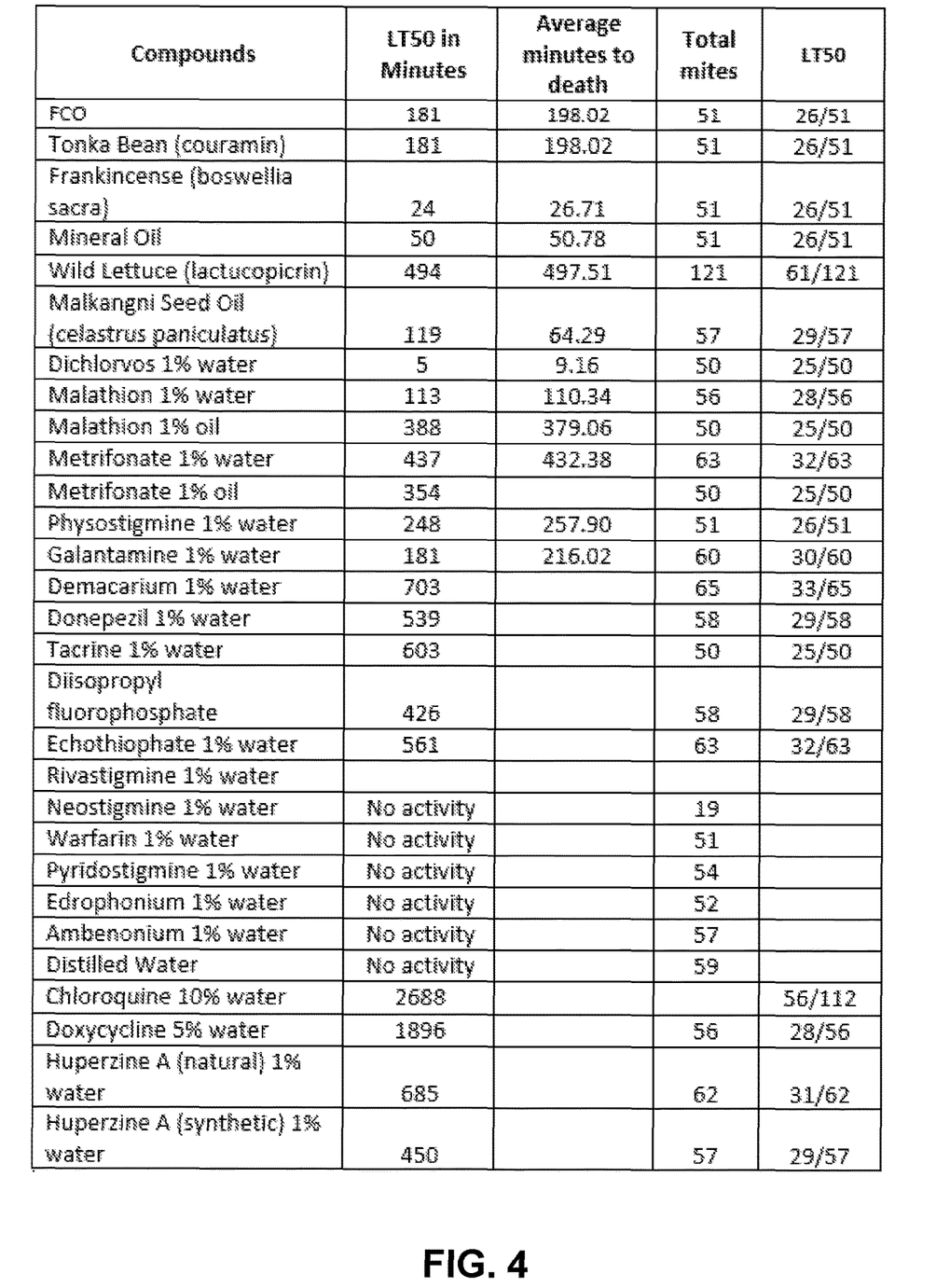
FIG. 4 is a table summary of Demodex survival time for various acetylcholinesterase inhibitors.

In vitro efficacy and mite lifetimes: Relative efficacy of various formulations are evaluated with a *Demodex* survival time experiments. FIG. 4 tabulates *Demodex* survival time, expressed in terms of LT50 (time at which 50% of *Demodex* mites are killed) and/or average minutes to death for various inhibitors.

We claim:

1. A method of treating an ophthalmological affliction, the method comprising the step of orally administering or topically applying to an individual having the ophthalmological affliction an acetylcholinesterase inhibitor in a dosage sufficient to inactivate *Demodex brevis* and/or *Demodex folliculorum* mites from hair follicles, skin, eyes, eyelids, eyelashes, or meibomian glands of the individual, resulting in amelioration or cessation of the manifestations of allergic and/or inflammatory responses to the mites that cause symptoms and signs of the ophthalmological affliction in the individual;
   wherein the individual is a human and the acetylcholinesterase inhibitor is selected from the group consisting of:
   physostigmine, demecarium, donepezil, tacrine, echothiophate, diisopropyl fluorophosphate, lactucopicrin, *Boswellia, Celastrus paniculatus*, coumarins, galantamine, huperzine A, and a prodrug or pharmaceutically acceptable salt thereof.

2. The method of claim 1, wherein said ophthalmological affliction is a *Demodex* induced inflammatory eye condition.

3. The method of claim 2, wherein said *Demodex* induced inflammatory eye condition is one or more of: Meibomian gland dysfunction, conjunctivitis, keratoconjunctivitis, hyperemia, dry eye, ocular rosacea and blepharitis.

4. The method of claim 1, wherein said acetylcholinesterase inhibitor is selected from the group consisting of: physostigmine, galantamine, demecarium, donepezil, tacrine, diisopropyl fluorophosphate, and echothiophate.

5. The method of claim 1, wherein said acetylcholinesterase inhibitor is efficiently transported into the epidermis or a subdermal region upon contact with said hair follicles, skin, eyes, eyelids, eyelashes, or meibomian glands of the individual.

6. The method of claim 1, wherein said step of orally administering or topically applying said acetylcholinesterase inhibitor kills or eliminates said *Demodex brevis* and/or *Demodex folliculorum* mites.

7. The method of claim 1, wherein the ophthalmological affliction affects the eye or eyelids, or both.

8. The method of claim 1, wherein said acetylcholinesterase inhibitor is selected from the group consisting of: huperzine A, galantamine, coumarins, *Celastrus paniculatus, Boswellia*; and a pharmaceutically acceptable salt thereof.

9. The method of claim 1, wherein the method of treating comprises the step of topically applying the acetylcholinesterase inhibitor, wherein the acetylcholinesterase inhibitor is formulated in a saline solution, carrier lotion, cream, soap, wash, shampoo or gel.

10. The method of claim 9, wherein a concentration of the acetylcholinesterase inhibitor in the topically applied carrier lotion, cream, soap, wash, shampoo or gel is about 0.001 to 5 percent by weight.

11. The method of claim 9, wherein a dosage of the acetylcholinesterase inhibitor in the topically applied carrier lotion, cream, soap, wash, shampoo or gel is less than about 150 mg/kg of body mass.

12. The method of claim 9, wherein the topically applied acetylcholinesterase inhibitor is applied to said hair follicles, skin, eyes, eyelids, eyelashes, or Meibomian Gland areas affected by the ophthalmological affliction.

13. The method of claim 1, wherein the topically applied acetylcholinesterase inhibitor is applied to an eye region corresponding to hair follicles, skin, eyes, eyelids, eyelashes, and/or meibomian gland areas at least once and not more than twice daily for a period of two to six weeks.

14. The method of claim 1, wherein the acetylcholinesterase inhibitor is orally administered or topically applied in a continued intermittent regime sufficient for prophylactic control of *Demodex* mite population in the hair follicles, skin, eyes, eyelids, eyelashes, or meibomian glands of the individual.

15. The method of claim 1, wherein the inactivation of the *Demodex brevis* and/or *Demodex folliculorum* mites from the said hair follicles, skin, eyes, eyelids, eyelashes, or meibomian glands of the individual results in a reduction in population of one or more bacteria in the said hair follicles, skin, eyes, eyelids, eyelashes, or meibomian glands of the individual.

16. A method of treating an ophthalmological affliction, the method comprising a step of topically applying to an eye region of an individual having the ophthalmological affliction that is a *Demodex*-induced inflammatory eye condition an active ingredient comprising an acetylcholinesterase inhibitor in a dosage sufficient to inactivate *Demodex brevis* and/or *Demodex folliculorum* mites from said eye region, wherein said eye region comprises hair follicles, skin, eyes, eyelids, eyelashes, or meibomian glands of the individual, resulting in amelioration or cessation of one or more manifestations of allergic and/or inflammatory responses to the mites that cause symptoms and signs of the ophthalmological affliction in the individual, wherein the topically applied active ingredient is applied to the said hair follicles, skin, eyes, eyelids, eyelashes, or meibomian glands areas affected by the ophthalmological affliction and to areas not affected by the ophthalmological affliction;

wherein the individual is a human and the acetylcholinesterase inhibitor is selected from the group consisting of:

physostigmine, demecarium, donepezil, tacrine, echothiophate, diisopropyl fluorophosphate, lactucopicrin, *Boswellia, Celastrus paniculatus*, coumarins, galantamine, huperzine A, and a prodrug or pharmaceutically acceptable salt thereof.

17. A method of treating an individual having a *Demodex* induced inflammatory eye condition, the method comprising the steps of:

applying to the individual in need thereof an acetycholinesterase inhibitor in a dosage sufficient to inactivate *Demodex brevis* mites and/or *Demodex folliculorum* mites from an eye region of the individual, wherein the eye region includes one or more of hair follicles, eyelids, eyelashes and Meibomian glands in and around an eye region;

wherein a sufficient amount of *Demodex brevis* mites and/or *Demodex folliculorum* mites are inactivated to ameliorate or cease manifestations of allergic and/or inflammatory responses to the *Demodex* mites that cause the inflammatory eye condition;

wherein the individual is a human and the acetylcholinesterase inhibitor is selected from the group consisting of:

physostigmine, demecarium, donepezil, tacrine, echothiophate, diisopropyl fluorophosphate, lactucopicrin, *Boswellia, Celastrus paniculatus*, coumarins, galantamine, and huperzine A, and a prodrug or a pharmaceutically acceptable salt thereof.

18. The method of claim 17, wherein the eye region corresponds to an area of between at least 1 cm and 10 cm around an outermost perimeter defined by the eye, eyelid, eyebrow and eyelashes.

* * * * *